United States Patent [19]
Brink

[11] Patent Number: 5,741,220
[45] Date of Patent: Apr. 21, 1998

[54] JOINT BRACE ASSEMBLY AND METHOD

[75] Inventor: N. Keith Brink, Oklahoma City, Okla.

[73] Assignee: Dura-Kold Corporation, Oklahoma City, Okla.

[21] Appl. No.: 633,571

[22] Filed: Apr. 17, 1996

[51] Int. Cl.$^6$ ................................. A61F 5/01; A61F 7/00
[52] U.S. Cl. .............................. 602/14; 602/26; 607/108; 607/112; 607/114
[58] Field of Search ..................................... 602/5, 14, 20, 602/23, 26, 60–63; 128/869, 878, 882; 607/96, 108, 112, 114

[56] References Cited

U.S. PATENT DOCUMENTS

| | | |
|---|---|---|
| 1,473,506 | 11/1923 | Nessler . |
| 1,567,931 | 12/1925 | Epler . |
| 1,927,751 | 9/1933 | Mensi . |
| 1,964,962 | 7/1934 | Rosenblum . |

(List continued on next page.)

FOREIGN PATENT DOCUMENTS

1185811  3/1970  United Kingdom .

OTHER PUBLICATIONS

Photographs #1–#5.
Dura*Kold Corporation brochure entitled "Re–usable Ice Wrap".
Dura*Kold Corporation brochure entitled "Re–usable Compression Ice Wraps".
Dura*Kold Corporation brochure entitled "Equine, Re–usable Compression Ice Wraps".
Elasto–Gel brand Cervical Collar advertisement entitled "Elasto–Gel Cervical Collar provides soothing relief for all your pains in the neck!"; Elasto–Gel brand Sinus Mask advertisement entitled Say goodbye to those excruciating sinus–triggered migraines!.
ErgoMed Inc. advertisement entitled "Only ErgoForm™ contoured cold packs fit the treatment to the trauma".
Icewrap™ brand advertisement entitled "Don't Miss Your Next Workout", from *Promises Kept* (Summer 1992).
Quinta—Group Limited brochure entitled "Mild Pack™ Micro–Crystalline Ice For Long Duration".
Physicians & Nurses Manufacturing Corporation brochure entitled "Cold Relief Pack".
Thera•P brand brochure entitled "Say goodbye to melting ice and dripping towels!".
Spenco® brand advertisement entitled "Spenco® Thermawrap™ Compress".
SmartPractice advertisment entitled "ThermoCare™ The All–In–One Hot And Cold Pack".
EBI© Medical Systems advertisement entitled "EBI© Temptek™ vs. Ice: Compare the Cold, Hard Facts", from *Orthopaedic Review*.
Breg™ brochure entitled "Polar Care™ Cold Therapy".
Cryo/Cuff™ brand brochure entitled "Cryo/Cuff™ compression dressings".
Guardian Products Inc. brochure entitled "I.C.E. Down© A Refreezable Flexible Cold Therapy Wrap".

*Primary Examiner*—Richard J. Apley
*Assistant Examiner*—Victor K. Hwang
*Attorney, Agent, or Firm*—McAfee & Taft

[57] ABSTRACT

A brace for a joint, such as a knee, is used with an underlying pad that extends continuously under the entire length of the brace. In use, the brace is secured to the pad such that a proximal portion of the brace engages an underlying proximal portion of the pad and such that a distal portion of the brace engages an underlying distal portion of the pad. A pouch with the pad removably receives one or more temperature packs to provide heat or cold therapy to the joint. The resulting assembly is such that access to the temperature pack(s) is available without removing either the brace or the pad from either the joint or the limb where the joint is. The pad forms part of a convertible therapeutic wrap which also includes indicia designating where the pad is to be cut to provide the pouch as a separate, smaller therapeutic wrap when the overall pad is not needed.

3 Claims, 3 Drawing Sheets

U.S. PATENT DOCUMENTS

| | | |
|---|---|---|
| 2,547,886 | 4/1951 | Poux . |
| 2,602,302 | 7/1952 | Poux . |
| 2,769,308 | 11/1956 | Krasno . |
| 2,800,456 | 7/1957 | Shepherd . |
| 2,984,839 | 5/1961 | Conrad et al. . |
| 3,149,943 | 9/1964 | Amador . |
| 3,429,138 | 2/1969 | Goldmerstein . |
| 3,463,161 | 8/1969 | Andrassy . |
| 3,491,761 | 1/1970 | Baker . |
| 3,500,014 | 3/1970 | Longo . |
| 3,506,013 | 4/1970 | Zdenek . |
| 3,802,215 | 4/1974 | Rowe . |
| 3,871,376 | 3/1975 | Kozak . |
| 3,889,684 | 6/1975 | Lebold . |
| 3,900,035 | 8/1975 | Welch et al. . |
| 3,913,559 | 10/1975 | Dandliker . |
| 3,950,789 | 4/1976 | Konz et al. . |
| 4,055,188 | 10/1977 | Pelton . |
| 4,081,150 | 3/1978 | Tyson . |
| 4,204,543 | 5/1980 | Henderson . |
| 4,324,111 | 4/1982 | Edwards . |
| 4,326,533 | 4/1982 | Henderson . |
| 4,381,025 | 4/1983 | Schooley . |
| 4,404,820 | 9/1983 | Romaine . |
| 4,513,053 | 4/1985 | Chen et al. . |
| 4,527,566 | 7/1985 | Abare . |
| 4,556,055 | 12/1985 | Bonner, Jr. . |
| 4,576,169 | 3/1986 | Williams . |
| 4,619,678 | 10/1986 | Rubin . |
| 4,625,729 | 12/1986 | Roney . |
| 4,628,932 | 12/1986 | Tampa . |
| 4,676,247 | 6/1987 | Van Cleve . |
| 4,688,572 | 8/1987 | Hubbard et al. .......................... 607/112 |
| 4,700,706 | 10/1987 | Münch . |
| 4,832,030 | 5/1989 | DeCanto . |
| 4,832,031 | 5/1989 | Last ...................... 607/114 X |
| 4,887,590 | 12/1989 | Logue et al. ................. 602/26 |
| 4,931,333 | 6/1990 | Henry . |
| 4,938,207 | 7/1990 | Vargo ........................ 602/26 |
| 4,941,462 | 7/1990 | Lindberg ................. 602/26 X |
| 4,981,135 | 1/1991 | Hardy ................. 607/114 X |
| 5,005,374 | 4/1991 | Spitlar . |
| 5,069,208 | 12/1991 | Noppel et al. . |
| 5,353,975 | 10/1994 | Libertucci . |
| 5,391,198 | 2/1995 | Cheney, III et al. . |
| 5,395,399 | 3/1995 | Rosenwald . |
| 5,415,624 | 5/1995 | Williams ................. 607/114 X |
| 5,443,488 | 8/1995 | Namenye et al. ................... 607/114 X |
| 5,462,517 | 10/1995 | Mann ........................ 602/26 |
| 5,484,448 | 1/1996 | Steele et al. . |
| 5,496,358 | 3/1996 | Rosenwald ......................... 607/114 X |
| 5,507,793 | 4/1996 | Hodges . |

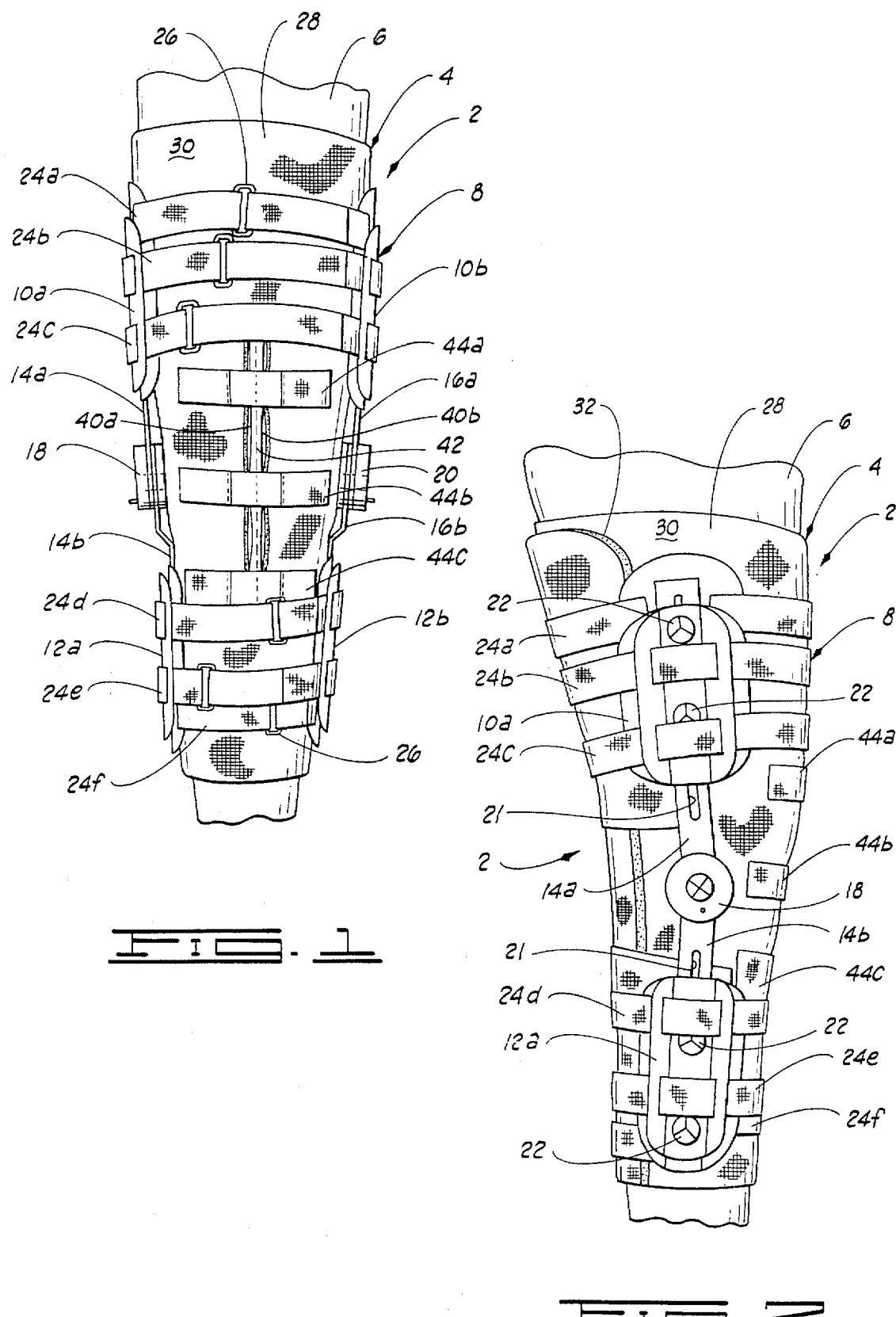

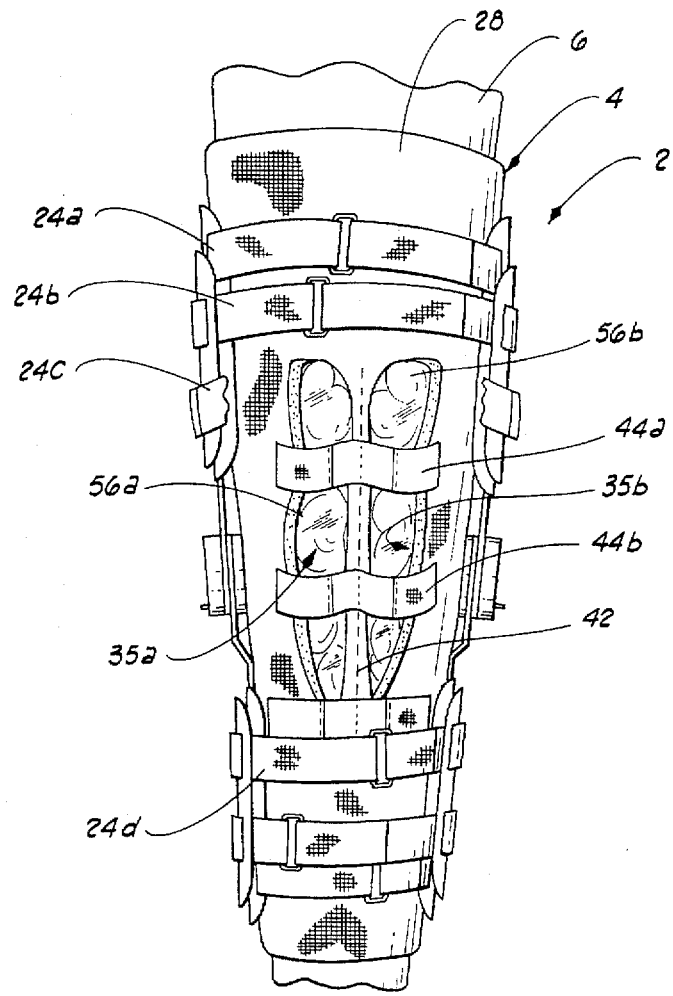
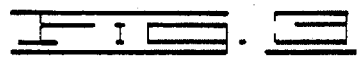
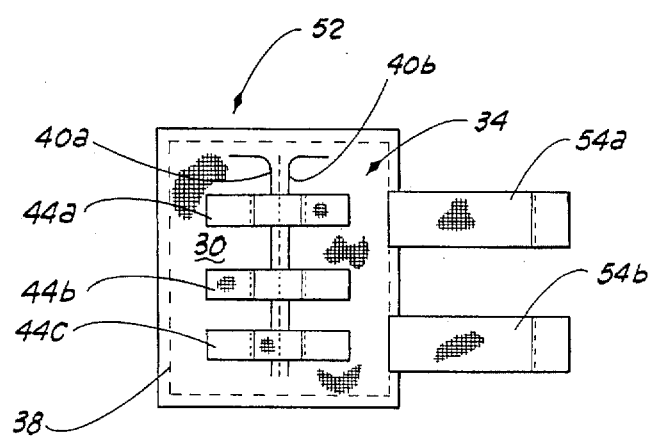
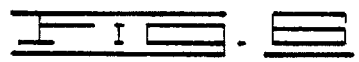

JOINT BRACE ASSEMBLY AND METHOD

BACKGROUND OF THE INVENTION

This invention relates to brace assemblies for a joint in a human or animal limb, such as a human knee. The invention also relates to methods for bracing such joints.

Sometimes when injuries occur at or near joints in limbs of humans or animals, such as with an injury to an anterior cruciate ligament at a human knee, the joint needs to be immobilized or its range of motion restricted during convalescence or rehabilitation. This is achieved with a brace mounted on the limb in proper orientation relative to the joint. Braces typically have proximal and distal members through which compression against the limb is applied to hold the brace on the limb. To alleviate pain that could result if such compressive members of the brace were directly against the skin of the limb, foam pads or the like are placed between the limb and the brace. There are typically multiple pads, with at least one underneath the proximal compression member and at least one underneath the distal compression member.

During at least the convalescence or rehabilitation period, it is usually desirable to apply heat or cold therapy to the joint (more specifically, the injury situs at or near the joint). This is achieved by some type of temperature treatment appliance used in conjunction with the brace. With a conventional ice bag as the temperature treatment appliance, the ice melts and needs to be replaced if cooling is to be maintained. Likewise, a hot water bottle (or other water-heated heat modality) needs to be refilled with hot water after a period of time.

Another type of temperature treatment appliance includes foam, elastic or nylon wraps designed to wrap around various body parts and to secure thereto with elastic straps and hook-and-pile fasteners. These have interior compartments that hold hot or cold members providing the temperature therapy. These compartments must be accessed to retrieve and replace the hot or cold members. If such a wrap must be partially disconnected or completely removed whereby the wrap is displaced relative to the body portion undergoing treatment, this would be inconvenient for the user, particularly if the wrap were applied over surgical dressings or underneath a brace. Because braces are held in place by straps, etc., they too would have to be partially undone or completely removed to get to the underneath wrap. This can also be uncomfortable, painful or damaging to the patient. For example, edema may occur at the site of the injury, and this condition causes pain and makes the patient uncomfortable when the affected area has to be moved to replace a therapeutic wrap. An improvement over the foregoing type of wrap is disclosed in U.S. patent application Ser. No. 08/537,347 filed Sep. 29, 1995 and incorporated herein by reference.

Still another type of temperature treatment appliance includes systems that circulate liquid through a member secured to the body part. These provide heat or cold therapy without having to move the member by which the temperature agent is applied to the body part. In such a system, a member containing a fluid circuit is secured to the body part and a heated or cooled liquid is circulated from a pump or gravity-feed device. This does not require any disconnection or displacement of the member to maintain the desired temperature agent in the member since the agent is continuously provided from the external source. This type of system is, however, significantly more expensive than a self-contained wrap of the type mentioned in the previous paragraph. It is also less convenient should the patient need to be moved from one location to another.

Any of the foregoing types of temperature treatment appliances can be combined with a brace. Despite this, there is still the need for an improved brace assembly and method of treating a joint with heat or cold therapy. Such assembly and method should utilize a discrete temperature pack to overcome disadvantages of the aforementioned flow type of appliance, and the assembly and method should also eliminate the need for additional, multiple cushioning elements for the brace. There is also the need for such assembly and method to provide continuous support for the joint whereby the discrete temperature pack can be used and removed without removing the brace. There is the further need for such assembly and method to be useful throughout any range of motion permitted by the brace. Because there is typically a continuing need for heat or cold therapy even after convalescence or rehabilitation, there is the need for the assembly and method to provide for a smaller therapeutic wrap that can be used and reused even after the brace is no longer needed.

SUMMARY OF THE INVENTION

The present invention overcomes the above-noted and other shortcomings of the prior art by providing a novel and improved joint brace assembly and method that accommodate one or more discrete temperature packs which are accessible without removing the invention from the limb to which it is connected when in use. Another aspect of the present invention is a novel and improved convertible therapeutic wrap which provides full-length coverage under a brace of the assembly and method, but which also provides for a separate, smaller therapeutic wrap; therefore, the convertible therapeutic wrap provides for simple ongoing heat or cold therapy even after the overall brace assembly or method are no longer needed. The present invention is useful throughout any range of motion permitted by the brace. The present invention has a simple implementation with no connections to external heating or cooling equipment.

The joint brace assembly of the present invention comprises a brace and a therapeutic wrap. The brace includes: proximal support means for supporting the brace against a jointed limb proximally of the joint; distal support means for supporting the brace against the limb distally of the joint; brace means connecting the proximal support means and the distal support means so that the proximal support means and the distal support means are spaced up to a maximum distance apart; and means for securing the brace means to the limb so that the proximal support means and the distal support means support the brace on opposite sides of the joint. The therapeutic wrap includes: an integral pad having a length at least equal to the maximum distance between the proximal and distal support means; means for securing the pad on the limb on opposite sides of the joint such that one end of the pad underlies the proximal support means and another end of the pad underlies the distal support means when the joint brace assembly is mounted on the limb; and pouch means defined with the pad for removably receiving a temperature pack to provide heat or cold therapy to the joint of the limb. Preferably, the pouch means is defined with the pad such that the pouch means is accessible without removing either the brace or the therapeutic wrap from the limb, whereby a temperature pack is insertable into and removable from the pouch means without removing either the brace or the therapeutic wrap from the limb.

The present invention also provides a method of treating a joint with heat or cold therapy. This method comprises mounting a pad on a limb of a body such that a joint in the limb is encased within a middle portion of the pad, wherein a chamber is defined at the middle portion of the pad for receiving a discrete temperature pack. The method further comprises securing a brace to the pad such that a proximal portion of the brace engages an underlying proximal portion of the pad and such that a distal portion of the brace engages an underlying distal portion of the pad. This method may further comprise inserting and removing a temperature pack relative to the chamber without removing either the brace or the pad from its placement relative to the limb. This method may still further include: removing the brace from the pad; removing the pad from the limb; and cutting the pad to provide a smaller therapeutic wrap for use on the body independently of the brace.

Therefore, from the foregoing, it is a general object of the present invention to provide a novel and improved joint brace assembly and method. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a front view of a preferred embodiment of the joint brace assembly of the present invention shown mounted on a leg to brace the knee of the leg.

FIG. 2 is a side view of the brace assembly of FIG. 1.

FIG. 3 is a front view of the brace assembly of FIG. 1 showing a pouch opened without having to remove the brace assembly from the leg.

FIG. 6 is a front plan view of a separate, smaller therapeutic wrap converted out of the wrap shown in FIGS. 4 and 5.

DETAILED DESCRIPTION OF PREFERRED EMBODIMENTS

U.S. patent application Ser. No. 08/537,347 filed Sep. 29, 1995, entitled "Therapeutic Wrap", and U.S. patent application Ser. No. 08/590,141 filed Jan. 23, 1996, entitled "Reusable Hot/Cold Temperature Pack, and Method of Manufacture", are incorporated herein by reference.

Figure 4:
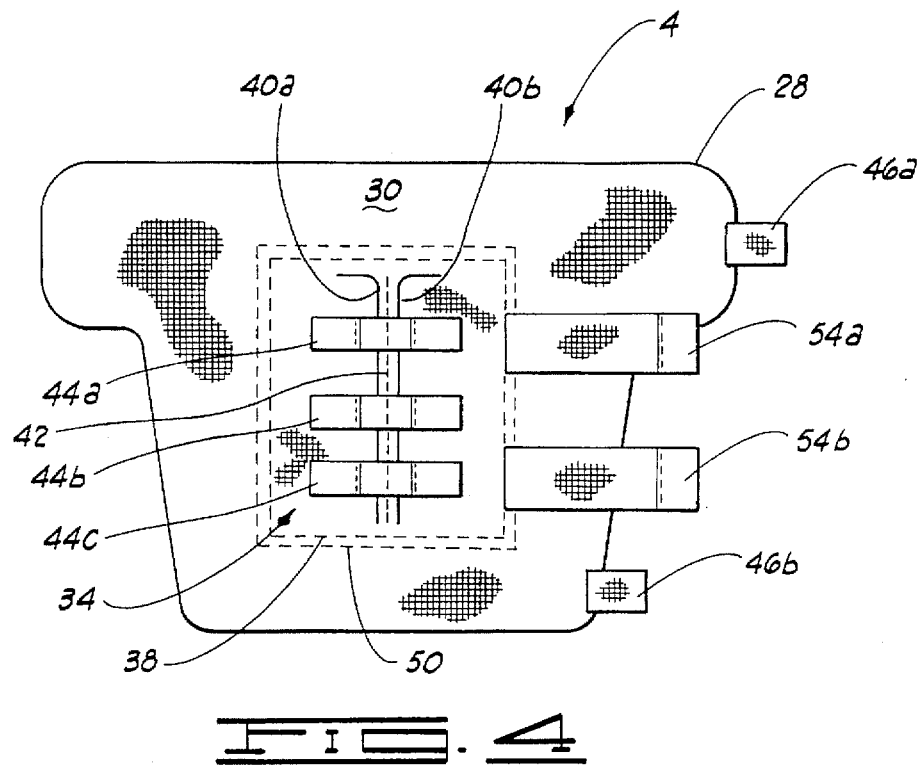
FIG. 4 is a front plan view of a convertible therapeutic wrap of the present invention.
Figure 5:
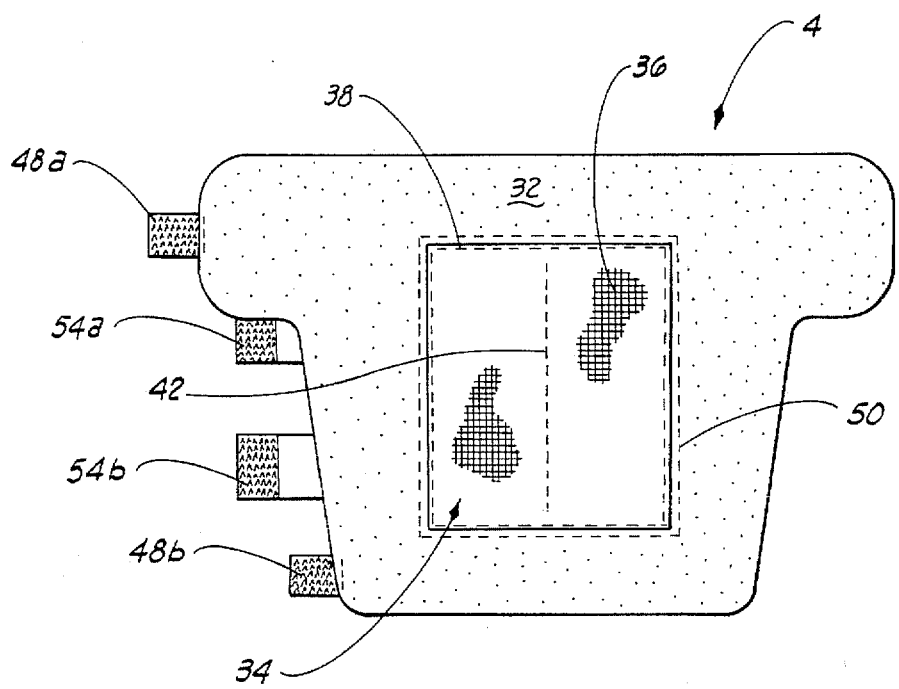
FIG. 5 is a rear plan view of the convertible therapeutic wrap shown in FIG. 4.

A joint brace assembly 2 of the present invention is shown in FIGS. 1-3; and a convertible therapeutic wrap 4 of the present invention, which is included in the assembly of FIGS. 1-3, is more clearly shown in FIGS. 4 and 5. These aspects of the present invention are illustrated with reference to use on a human leg 6 during convalescence or rehabilitation of the knee of the leg; however, the present invention is not limited to such use.

The joint brace assembly 2 includes a brace 8. The illustrated brace 8 includes proximal support means for supporting the brace against the limb having the joint relative to which the brace is to be applied. The proximal support means provides its support proximally of the joint. This is implemented in the illustrated embodiment by oppositely positioned compression members 10a, 10b shown in FIGS. 1-3.

The brace 8 also includes distal support means for supporting the brace against the limb distally of the joint. In the illustrated embodiment of FIGS. 1-3, this includes oppositely positioned compression members 12a, 12b.

The compression members 10, 12 are slidably mounted in the illustrated embodiment on brace means which connect the proximal support means and the distal support means so that these two support means are spaced up to a maximum longitudinal (i.e., along the length of the limb) distance apart. The brace means of the illustrated embodiment includes rigid structural member pairs 14a, 14b and 16a, 16b. The members 14a, 14b are pivotally connected at a hinge defined by a range of motion connector 18. The structural members 16a, 16b are likewise connected in this manner by a range of motion connector 20. Referring to FIG. 2, slots 21 in each of the structural members 14, 16 receive slide pins or brackets of the compression members 10, 12 so that the compression members can slide relative to the respective structural members but can be secured thereto by appropriate operation of knobs 22 connected to the slide pins or brackets (not shown).

The brace 8 also includes means for securing the brace means to the limb so that the proximal support means and the distal support means support the brace on opposite sides of the joint. This includes straps 24 as shown in FIGS. 1-3. Each strap passes through slots in the respective compression members 10, 12. One end of each strap 24 has a loop or ring 26 through which the other end of the strap passes and then doubles back to secure to itself with a hook tab on such other end of the strap. Each strap 24 is thus preferably made of a pile material to secure with the hook tab.

The brace 8 as described above is a known apparatus used in a known manner. One particular implementation is the "REHAB³" knee brace from Orthopedic Technology, Inc. of Tracy, Calif. Other particular implementations and types of braces can be used so long as they include the general elements of proximal support means, distal support means, interconnecting brace means, and means for securing the brace to the limb.

The joint brace assembly 2 of the present invention also includes a therapeutic wrap, which is particularly implemented in the preferred embodiment by the convertible therapeutic wrap 4.

The convertible therapeutic wrap 4 includes a pad 28 more clearly shown in FIGS. 4 and 5. The pad 28 has a hook-sensitive side 30 (FIG. 4) laminated to a foam substrate defining a side 32 (FIG. 5) of the pad 28. This construction provides comfort, stability and insulation. A particular type of material is the foam and pile material used in prior therapeutic wrap products from Dura-Kold Corporation of Oklahoma City, Okla. For the particular implementation of FIGS. 4 and 5, the pad 28 has a substantially T shape with the wider upper portion as viewed in the drawings defining the portion underlying the proximal end of the brace 8 in FIGS. 1-3. The pad 28 of this implementation is integral throughout its length. Its length is at least equal to the maximum distance between the outer portions of the compression members 10, 12 so that only the single pad 28 is needed as the cushion between the proximal and distal compression members 10, 12 and the leg 6. The intermediate continuity of the pad 28 provides cushioning relative to the range of motion hinges 18, 20. The compression members 10, 12 and the hinges 18, 20 have hook elements which attach to the pile material of the side 30 of the pad 28 when the joint brace assembly 2 is used as in FIGS. 1-3.

The wrap 4 also includes a container 34. The container 34 is constructed so that it can receive a discrete temperature member to provide heat or cold to an adjacent body portion and so that it can conform to the body portion when the wrap 4 is connected thereto. The temperature member itself does not form a part of the present invention but can be implemented by any suitable means providing either heat or cold as desired. For example, ice cubes or artificial ice products can provide the temperature member when cold is desired. A gel pack is another non-limiting example. When cold is desired, a preferred implementation is the mat-type or combination mat/gel cold pack used in products sold by Dura-Kold Corporation; however, the wrap 4 is preferably adapted so that it can receive various types of heating or cooling products, thereby providing the wrap 4 with a versatility in that it is not limited to use with a single type of heating or cooling product. This versatility does not, however, include use of the wrap 4 as a direct part of a flow type system described above. That is, the therapeutic wrap 4 of the present invention is not connected to any external temperature source, but rather wholly contains the temperature source(s) within itself.

The container 34 is specifically implemented as a flexible pouch having at least one chamber defined therein. In the illustrated pouch 34, two chambers 35 are defined (see FIG. 3). The pouch of the preferred embodiment includes a side defined by a portion of the pad 28 and a side defined by a lightweight mesh 36 (FIG. 5) that offers a temperature barrier but also is porous enough to allow the temperature flow that is needed to provide the desired treatment. The mesh side 36 forms a layer between the foam substrate of the pad 28 and the skin of the patient to which the wrap 4 is connected. Examples of this mesh material include nylon, acetate, polyester or any other suitable material with porous qualities. The selected material preferably is of a type that wicks away any condensation that may occur. A particular type is that used in prior therapeutic wraps from Dura-Kold Corporation.

At least when a self-contained temperature member (e.g., the above-mentioned mat-type cold pack product) is used with the wrap 4, the materials of the sides of the pouch 34 need not define it as being watertight or waterproof, which it clearly will not be if open-pore mesh material is used as referred to above.

The material of mesh side 36 and the material of the pad 28 are joined by stitching 38 (FIGS. 4 and 5) sewn around the periphery of the pouch 34. Other means for attaching the sides can be used. Non-limiting examples include heat or fusion processes.

The side of the pouch 34 defined by part of the pad 28 has openings into each of the chambers. The openings into the chambers are defined by respective slits 40a, 40b (FIG. 4) formed, such as by cutting, through the pad 28. The main portions of the slits 40a, 40b are transverse to the wrapping direction of the container 34. Preferably, the slits 40 are perpendicular or at least substantially transverse to the direction of wrap so that the slits do not substantially curve along the direction of wrap, thereby facilitating access into the chamber with the respective slit to insert or remove the temperature mass without disconnecting the pouch 34 or the overall wrap 4 from the body. In the illustrated embodiment, the slits 40a, 40b are longitudinal and parallel to each other and spaced near each other at the middle of the wrapping direction dimension of the container 34.

Each slit 40a, 40b defines an elongated portal through which ingress and egress into and out of the respective chamber is permitted. The remaining perimeters of the respective chambers are closed to outside access. Thus, in the illustrated preferred embodiment the temperature means can be inserted and extracted relative to a chamber only through the respective slit.

Stitching 42 (FIGS. 4 and 5) across the middle of the pouch 34 joins the pad 28 and the mesh 36 and divides the two adjacent chambers. This stitching 42 also holds butterfly slit closure straps 44 as shown in FIG. 1. The chamber closure straps 44 of the preferred embodiment have elastic material sewn to quick release hook material which engages the pile material of the pad side of the pouch 34 to close the openings into the chambers so that the hot or cold elements are retained inside the chambers. The elasticity of the straps 44 allows them to expand and contract as the knee is pivoted if movement of the knee is permitted by the settings of the range of motion connectors 18, 20; therefore, the wrap 4 accommodates flexion and extension of the limb at the covered joint.

The therapeutic wrap 4 further includes means for securing the pad 28 on the leg (or other limb) on opposite sides of the knee (or other joint) such that one end of the pad 28 underlies the proximal support means and another end of the pad 28 underlies the distal support means when the assembly 2 is mounted on the limb as illustrated in FIGS. 1–3. This securing means includes, in the illustrated embodiment, straps 46a, 46b. Each of the straps 46 has a fixed end connected to a respective edge of the pad 28. Each strap 46 also has a free end adapted to connect to the pad 28 so that the respective strap 46 secures the pad 28 to the body without obstructing access through the slits 40 and without obstructing operation of slit or chamber closure straps 44. Thus, each strap 46 has one end fixed to one side of the openings defined by the slits 40 and another end adapted to releasably connect to the pad 28 on another side of the openings after the free end is extended around the portion of the body where the wrap 4 is to be mounted. Other releasable connector means embodiments can, of course, be used whether they are of a strap or non-strap type (e.g., another strap type connector is to have the straps 42 formed as integral parts of and of the same material as the pile side of the pad 28).

The wrap securing straps 46 of the illustrated embodiment are made of an elastic material to which hook containing members 48 (FIG. 5) are attached at the straps' free ends. The hook elements of the members 48 releasably connect to the pile surface of the pile side 30 of the pad 28. The elastic of the straps 46 allows the product to be used around different sizes of body portions and minimizes any tourniquet effect; however, elasticity is not required or a limitation of the invention (e.g., if the straps are implemented as integral with and made of the pile material, there would not be substantial elasticity in such straps). The fixed ends of the straps 46 are sewn along one edge of the pad 28 as shown in the drawings. The straps 46 are parallel to each other and extend in the direction of wrap in the illustrated embodiments.

The therapeutic wrap 4 further includes indicia referring to or designating a cutting perimeter along which the pad 28 is defined to be cut to produce a separate smaller therapeutic wrap for use without the brace 8. The indicia means can include written instructions, a template, some marking fixed to the pad, or other suitable indicator for cutting. In the illustrated preferred embodiment, the indicia means is applied to the pad 28 to mark a cut line outside a periphery of the pouch 34. Specifically, this indicia means includes thread 50 stitched to the pad 28 outwardly from the stitching 38 so that, preferably, it does not also stitch the material 36. The thread 50 should be distinctive such that it is apparent where to cut; however, this does not mean the thread 50 is necessarily of different color or type from thread used for other stitching on the wrap. When the pad 28 is cut along this line, a separate smaller therapeutic wrap 52 shown in FIG. 6 results.

The therapeutic wrap 4 still further includes means for securing the smaller therapeutic wrap 52 to a body portion. In the illustrated embodiment, this includes straps 54 having the same elastic and hook components as the straps 46 and sewn at one end of the wrap 52 by the stitching 38. In the illustrated embodiment the straps 54 are also used in securing the larger pad 28 to the limb.

The method of the present invention is for treating a joint with heat or cold therapy. This includes mounting the pad 28 on a limb of a body such that a joint in the limb is encased within a middle portion of the pad. One or more chambers are defined by the pouch 34 at the middle portion of the pad 28 for receiving one or more discrete temperature packs. The method also includes securing the brace 8 to the pad 28 such that the proximal portion of the brace 8 engages the underlying proximal portion of the pad 28 and such that the distal portion of the brace 8 engages the underlying distal portion of the pad 28. Such connection of the brace 8 itself and its operation are as known in the art.

The method further comprises inserting and removing one or more temperature packs relative to the chamber without removing either the brace 8 or the pad 28 from its placement relative to the limb. Referring to FIG. 3, once the wrap 4 is secured to the body portion by (1) laying the pad 28 at the place of application, (2) extending the straps 46 (and 54 if desired) and (3) attaching the hook material of the straps 46 (54) to the pile material of the pad 28, the chambers of the pouch 34 can still be readily accessed. The chambers lie on opposite sides of a fold line defined between the slits 40a, 40b substantially in conjunction with stitch line 42. This fold line overlies the knee's patella and the chambers thus overlie opposite sides of the knee joint where the heat or cold is to be applied. Access to a chamber is accomplished by lifting the respective end tabs of the chamber closure straps 44 and peeling the material of this portion of the pad 28 back at the respective slit 40. One's hand can then be inserted into the chamber to grasp the temperature element to pull it from the chamber. Insertion of the material is performed in a like manner. When the temperature element is in place in the chamber (as illustrated by temperature packs 56 for the two chambers in FIG. 3), the material of the pad 28 is folded back down to close the slit 40 and the respective end tabs of the straps 44 are pressed down to secure to the pile material of the pad 28.

From FIG. 3 it will be noted that it is important for the slits 40 to run substantially parallel to the length of the limb to which the wrap 4 is attached. If the slits 40 were formed along the direction of wrap around the knee, the slits would curve around the circumference of the limb so that it would be difficult to insert or extract the temperature elements 56 without removing or otherwise loosening the wrap 4 or the brace 8.

FIG. 3 also illustrates that the present invention is effective even if the brace 8 needs to be partially unstrapped, as illustrated by the disconnected strap 24c; however, this does not change the positioning of either the wrap 4 or the brace 8 relative to the limb 6.

The method still further comprises removing the brace 8 from the pad 28 by disconnecting all the straps 24, removing the pad 28 from the limb 6 by disconnecting the straps 46 (and 54 if used), and cutting the pad 28 to provide the smaller therapeutic wrap 52 for use on the body independently of the brace 8. For the embodiment shown in FIG. 4, this includes cutting, such as with scissors or other suitable implement, along the stitch line 50. It could include freehand cutting in response to indicia defined by an instruction sheet accompanying the wrap or cutting in response to a template provided for the wrap or by other means. The separated wrap 52 is used in the same known manner as other wraps of its type, such as those from Dura-Kold Corporation.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A joint brace assembly, comprising:

a brace, including:
  proximal support means for supporting said brace against a jointed limb proximally of the joint;
  distal support means for supporting said brace against the limb distally of the joint;
  brace means connecting said proximal support means and said distal support means so that said proximal support means and said distal support means are spaced up to a maximum distance apart; and
  means for securing said brace means to the limb so that said proximal support means and said distal support means support said brace on opposite sides of the joint; and a therapeutic wrap including:
  an integral pad having a length at least equal to said maximum distance;
  means for securing said pad on the limb on opposite sides of the joint such that one end of said pad underlies said proximal support means and another end of said pad underlies said distal support means when said joint brace assembly is mounted on the limb;
  a pouch defined with said pad for removably receiving a temperature pack to provide heat or cold therapy to the joint of the limb;
  indicia on said pad defining a cutting perimeter along which said pad is defined to be cut to produce a smaller therapeutic wrap for use without said brace; and
  means, connected to said portion of said pad included in said smaller therapeutic wrap, for securing said smaller therapeutic wrap to a body portion.

2. A method of treating a joint with heat or cold therapy, comprising:

mounting a pad on a limb of a body such that a joint in the limb is encased within a middle portion of the pad, wherein a chamber is defined at the middle portion of the pad for receiving a discrete temperature pack;

securing a brace to the pad such that a proximal portion of the brace engages an underlying proximal portion of the pad and such that a distal portion of the brace engages an underlying distal portion of the pad; and inserting and removing a temperature pack relative to the chamber without removing either the brace or the pad from its placement relative to the limb.

3. A method of treating a joint with heat or cold therapy, comprising:

mounting a pad on a limb of a body such that a joint in the limb is encased within a middle portion of the pad, wherein a chamber is defined at the middle portion of the pad for receiving a discrete temperature pack;

securing a brace to the pad such that a proximal portion of the brace engages an underlying proximal portion of the pad and such that a distal portion of the brace engages an underlying distal portion of the pad;

removing the brace from the pad;

removing the pad from the limb; and cutting the pad to provide a smaller therapeutic wrap for use on the body independently of the brace.

* * * * *